(12) United States Patent
Shizuya

(10) Patent No.: US 6,991,900 B2
(45) Date of Patent: Jan. 31, 2006

(54) METHODS FOR IDENTIFYING AN ESSENTIAL GENE IN A PROKARYOTIC MICROORGANISM

(75) Inventor: Hiroaki Shizuya, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 319 days.

(21) Appl. No.: 09/896,509

(22) Filed: Jun. 28, 2001

(65) Prior Publication Data
US 2002/0127562 A1   Sep. 12, 2002

Related U.S. Application Data

(60) Provisional application No. 60/214,621, filed on Jun. 28, 2000.

(51) Int. Cl.
C12Q 1/68      (2006.01)
C12Q 1/18      (2006.01)
C12N 15/74     (2006.01)
C12N 15/00     (2006.01)
A01N 63/00     (2006.01)

(52) U.S. Cl. .................... 435/6; 435/473; 435/476; 435/32; 435/69.1; 435/320.1; 435/474; 435/475; 435/183; 424/93.2

(58) Field of Classification Search ............ 435/6, 435/473, 32, 69.1, 320.1, 325, 183, 476, 435/474, 475; 536/23.2, 29.2; 530/350; 424/93, 2
See application file for complete search history.

(56) References Cited

U.S. PATENT DOCUMENTS

| | | | |
|---|---|---|---|
| 5,677,170 A | | 10/1997 | Devine et al. |
| 5,843,772 A | | 12/1998 | Devine et al. |
| 6,673,567 B2 | * | 1/2004 | Sharpe et al. ............... 435/29 |

OTHER PUBLICATIONS

Kim, Ung-Jin et al., "Construction and Characterization of a Human Bacterial Artificial Chromosome Library," *Genomics*, vol. 34, 1996, pp. 213-218.

Shizuya, Hiroaki and Kouros-Mehr, Hosein, "The Development and Applications of the Bacterial Artificial Chromosome Cloning System," Keio Journal of Medicine, Vol. 50, No. 1, Mar. 2001, pp. 26-30.

* cited by examiner

*Primary Examiner*—Terry McKelvey
*Assistant Examiner*—Maria Marvich
(74) *Attorney, Agent, or Firm*—DLA Piper Rudnick Gray Cary US LLP

(57) ABSTRACT

Methods are provided for the rapid identification of essential or conditionally essential DNA segments in any species of haploid cell (one copy chromosome per cell) that is capable of being transformed by artificial means and is capable of undergoing DNA recombination. This system offers an enhanced means of identifying essential function genes in diploid pathogens, such as gram-negative and gram-positive bacteria.

54 Claims, 3 Drawing Sheets

Fig. 1. Diagram of the introduction and the elimination of Tn5 transposon and BACts in *E. coli*

METHODS FOR IDENTIFYING AN ESSENTIAL GENE IN A PROKARYOTIC MICROORGANISM

This application claims priority under 35 U.S.C. § 119(e)(1) to U.S. provisional application Ser. No. 60/214,621, filed Jun. 28, 2000, which is incorporated by reference herein in its entirety.

This invention was made in part with government support under Department of Energy Grant No. DE-FG03-99ER62855/S-95,206. The government has certain rights in this invention.

BACKGROUND OF THE INVENTION

1. Field of the Invention

The present invention relates generally to genetically engineered cells, and more specifically, to the study of essential genes in prokaryotic microorganisms.

2. Background Information

The discovery and development of drugs able to prevent and cure bacterial infections have represented one of the Twentieth Century's major contributions toward improving human longevity and quality of life. Antibacterial agents are among the most commonly prescribed drugs of any kind worldwide. Used properly and appropriately, these drugs are lifesaving. However, their indiscriminate use drives of the cost of health care and leads to bacterial resistance that renders valuable drugs useless. The rational use of antibacterial agents is dependent, among others, on an understanding of their mechanisms of action and bacterial strategies for resistance to drugs.

Antibacterial agents, like all anti-microbial drugs, are directed against unique targets not present in mammalian cells. The goal is to limit toxicity to the host and maximize chemotherapeutic activity affecting invading microbes only. One major difference between bacterial and mammalian cells i the presence in bacteria of a rigid wall external to the cell membrane. The wall protects bacterial cells from osmotic rupture because of the difference between the hyperosmolar (up to 20 atm) cell interior and the usually isosmolar or hyposmolar host environment. In both gram-positive and gram-negative bacteria, peptidoglycan, a large, covalently linked sacculus that surrounds the bacterium, is the structure that confers cell wall rigidity and resistance to osmotic lysis. In gram positive bacteria, peptidoglycan is the only later external to the cell membrane and is thick) 20 to 80 nm); while in gram-negative bacteria the peptidoglycan layer is thin (1 nm) and is protected by an outer membrane. Chemotherapeutic agents directed at any stage of the synthesis, export, assembly, or cross-linking of peptidoglycan inhibit bacterial cell growth and, in most cases, lead to cell death.

Bacitracin, a cyclic peptide antibiotic, inhibits the conversion to its active form of the lipid carrier that moves the water-soluble cytoplasmic peptidoglycan subunits through the cell membrane to the cell exterior. Cell wall subunits accumulate in the cytoplasm and can be added to the growing peptidoglycan chain.

Cyclopeptides, such as vancomycin and teichoplanin) are high molecular weight antibiotics that bind to the terminal D-alanine-D-alanine component of the stem peptide when the subunits are external to the cell membrane and still linked to the lipid carrier. This binding sterically inhibits the addition of sub units to the peptidoglycan backbone.

β-Lactam antibiotics, such as penicillins, cephalosporins, carbapenems, and monobactams, characterized by a four-membered β-Lactam ring, prevent the cross-linking reaction called transpeptidation. Energy for attaching a peptide cross-bridge from the stem peptide of one peptidoglycan subunit to another is derived from the cleavage of a terminal D-alanine residue from the subunit stem peptide. The β-Lactam ring of the antibiotic forms an irreversible covalent acyl bond with the transpeptidase enzyme, preventing the cross-linking reaction. Transpeptidases and similar enzymes involved in cross-linking are called penicillin-binding proteins because they have active sites that bind β-Lactam antibiotics.

Virtually all the antibiotics that inhibit bacterial cell wall synthesis are bactericidal, eventually resulting in the cell's death due to osmotic lysis. However, much of the loss of cell wall integrity following treatment with cell-active agents is due to the bacteria's own cell wall-remodeling enzymes (autolysins) that cleave peptidoglycan bonds in the normal course of cell growth. Autolysis without normal cell wall repair results in weakness and eventual cell death.

Most of the antibacterial agents that inhibit protein synthesis interact with the bacterial ribosome. The differences between the composition of bacterial and mammalian ribosomes give these compounds their selectivity. For example, aminoglycosides are a group of structurally related compounds containing three linked hexose sugars. Aminoglycosides exert a bactericidal effect by binding irreversibly to the 30 S subunit of the bacterial ribosomes and blocking initiation of protein synthesis. Macrolides and lincosamides, although structurally different, are two types of antibiotics that bind specifically to the 50 S portion of the bacterial ribosome. Chloramphenicol also binds irreversibly to the 50 S portion of the bacterial ribosome at a site close but not identical to the sites binding the macrolides and lincosamides. Tetracyclines interact reversibly with the bacterial 30 S ribosomal subunit, blocking the binding of aminoacyl tRNA to the mRNA-ribosome complex. This mechanism is markedly different from that of the aminoglycosides, which also bind to the 30 S subunit.

The antimetabolites are all synthetic compounds that interfere with bacterial synthesis of folic acid. Products of the folic acid synthesis pathway function as coenzymes for the one-carbon transfer reactions that are essential for the synthesis of thymidine, all purines, and several amino acids. Inhibition of folate synthesis leads to cessation of cell growth and in some cases, to bacterial cell death. The principal antibacterial antimetabolites are sulfonamides and trimethoprim.

Numerous additional antibacterial compounds have disparate effects on nucleic acids. The quinolones, including nalidixic acid and its fluorinated derivatives, are synthetic compounds that inhibit the activity of the A subunit of the bacterial enzyme DNA gyrase, which is responsible for negative supercoiling of DNA during replication in the intact cell. The antibiotic novobiocin also interferes with the activity of DNA gyrase, but it interferes with the B subunit. Rifampin, used primarily as an antituberculosis agent, binds tightly to bacterial DNA-dependent RNA polymerase, thus inhibiting transcription of DNA into RNA, and nitrofurantoin, a synthetic compound, causes DNA damage, being reduced by a bacterial enzyme to highly reactive, short-lived intermediates that are thought to cause DNA strand breakage.

Still other compounds cause alternation of cell membrane permeability. The polymyxins behave as cationic, surface-active compounds that disrupt the permeability of both the outer and the cytoplasmic membranes of gram-negative bacteria. Gramicidin A, on the other hand, acts as an ionophore, forming pores or channels in lipid bilayers.

One major and important class of genes consists of those bacterial genes that are essential for growth or viability of a bacterium. Because useful conventional antibiotics, such as those described above, are known to act by interfering with the products of essential genes, it is likely that the discovery of new essential gene products will have a significant impact on efforts to develop novel antimicrobial drugs.

Conditional mutations such as temperature or suppressor sensitive mutations have been used in the past to identify some of the essential genes in bacteria. However, not all essential genes can be identified by these types of mutations. The limitation is due to the fact that these conditional mutations must occur at a specific codon of the genes in order to alter the coded amino acid of the protein. Therefore, the occurrence of mutants with these phenotypes is expected to be low. Moreover, not all of the gene can be converted to conditional mutations; there may be no codon causing these mutations in their nucleotide sequences.

Essential gene products have been traditionally identified through the isolation of conditional lethal mutants, or by transposon mutagenesis in the presence of a complementing wild type allele (balanced lethality). However, such approaches are laborious, as they require identification, purification, and study of individual mutant strains. These methods are also limited to species with well-developed systems for genetic manipulation and, therefore, cannot be readily applied to many of the potentially dangerous microorganisms whose genomes have recently been sequenced.

For example, conditional mutations such as temperature or suppressor sensitive mutations have been used in the past to identify some of the essential genes in bacteria. However, not all of the essential genes can be identified by these types of mutations because the conditional mutation must occur at a specific codon of the genes in order to alter the coded amino acid of the protein. Therefore, the occurrence of mutants with these phenotypes is expected to be low. Moreover, not all of the gene can be converted to conditional mutations; there may be no codon causing the conditional mutation in the nucleotide sequences of the bacterial genome.

Thus, it can be seen that successful antibiotics are all compounds that in one way or another impair function of an essential gene in bacteria. Despite the great discoveries that have been made, there is great need for new and better antibiotic compounds for pharmaceutical use in the treatment of mammalian species, including farm animals, pets and humans and for development of laboratory methods useful in development of such new compounds. The present invention satisfies this need and provides additional advantages.

SUMMARY OF THE INVENTION

In one embodiment according to the present invention, there are provided methods for identifying an essential chromosomal gene in a haploid test organism utilizing a BAC-carrying merodiploid test cell constructed from a wild-type haploid host cell that is transformed with a bacterial artificial chromosome (BAC) carrying a segment of DNA of the haploid test organism. The segment of DNA in the BAC is homologous to a known segment of chromosomal DNA in the host cell and the BAC is engineered to be sensitive to an environmental condition that selectively prevents replication of the BAC in the host cell. A bacterial transposon is then inserted into the merodiploid test cell so as to disrupt function of a gene therein and one or more of the BAC-carrying merodiploid test cells are cultured in a suitable culture medium while introducing the environmental condition so as to transform the merodiploid test cells into haploid test cells. One or more of the haploid test cells that contain transposon-mutagenized DNA in an essential chromosomal gene therein are identified.

In another embodiment according to the present invention, there are provided methods for screening bacterial genes in a pathogenic bacterium whose genome is known to select compounds with putative antibiotic activity. In this embodiment, a BAC-carrying merodiploid test cell is constructed by transforming a wild-type haploid host cell with a BAC that carries a known segment of DNA of a pathogenic bacterium, which segment is homologous to a segment of chromosomal DNA in the host cell, and wherein the BAC in the test cell is sensitive to an environmental condition that selectively prevents replication of the BAC in the test cell. A transposon transposon is randomly inserted into the merodiploid test cell so as to disrupt function of a gene therein and one or more of the merodiploid test cells are cultured in a suitable culture medium while introducing the environmental condition. One or more test cells that do not survive subjection to the environmental condition are identified as containing the transposon in an essential chromosomal gene therein and a corresponding essential gene is obtained in the known segment of DNA of the pathogenic bacterium by homology with the identified essential chromosomal gene in the test cell. The corresponding essential gene obtained from the pathogenic bacterium or a bacterial protein encoded by the corresponding essential gene is screened against putative antibiotic compounds to determine those compounds that bind to or interrupt function of the corresponding essential gene or the bacterial protein. Such a compound is a candidate antibiotic against the pathogenic bacterium.

In yet another embodiment according to the present invention, there are provided methods for identifying an essential chromosomal gene in a haploid test organism. In this embodiment, the invention method comprises constructing a BAC carrying a known segment of DNA of the haploid test organism, which segment is homologous to a known segment of chromosomal DNA in a haploid host cell and randomly inserting a bacterial transposon into the BAC so as to disrupt function of a gene in the segment of chromosomal DNA. The BAC is then introduced into the haploid test cell to create a merodiploid test cell, the merodiploid test cell is cultured in a suitable culture medium, and one or more BAC-carrying merodiploid test cells that do not survive in culture is identified as containing the transposon in an essential chromosomal gene therein. Identity of the essential chromosomal gene is obtained by homology with the known segment of DNA inserted into the BAC that was introduced into the identified test cell.

DETAILED DESCRIPTION OF THE INVENTION

Figure 1:
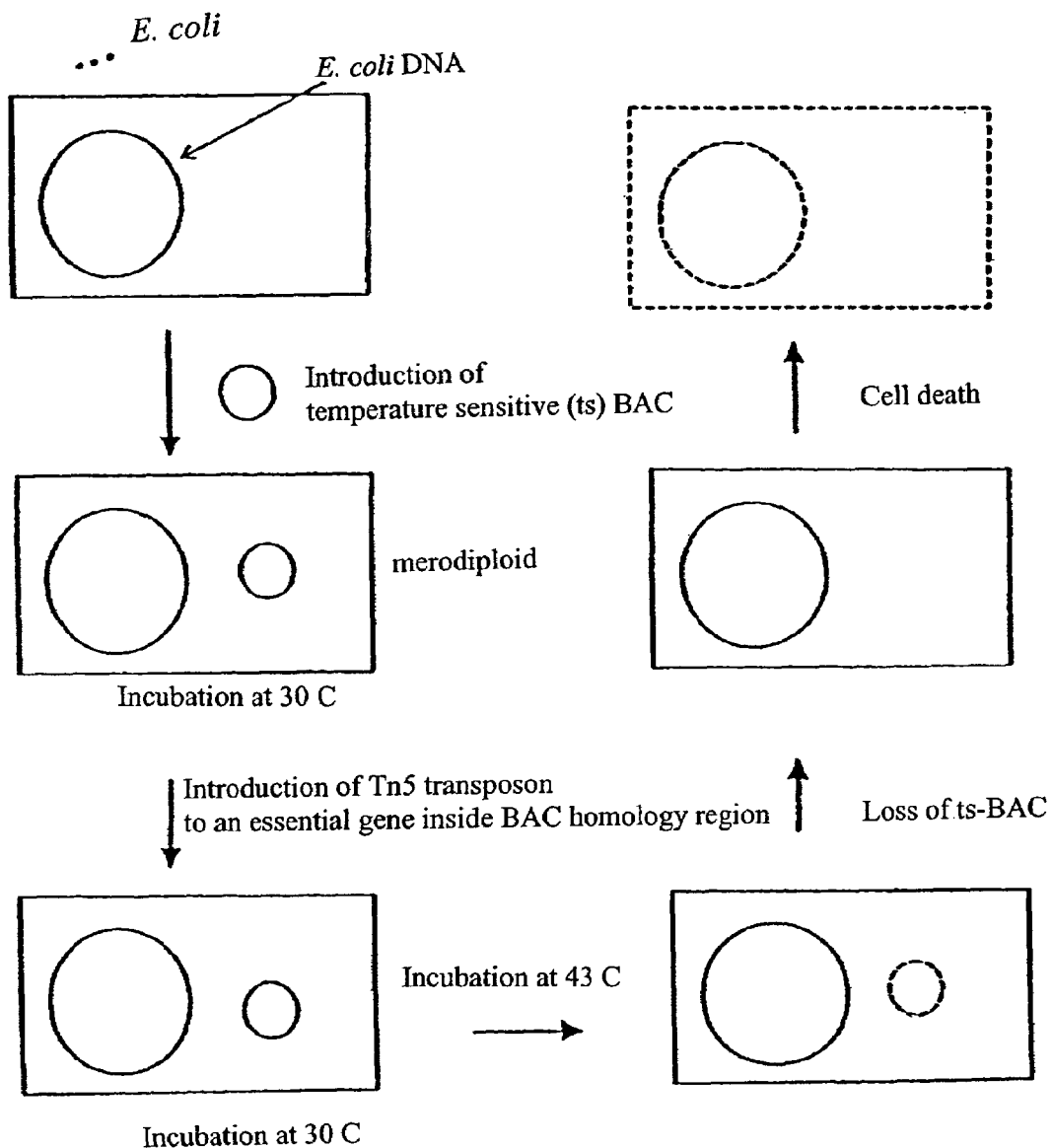
FIG. 1 is a schematic diagram of the invention method wherein an *E. coli* host cell is transfected with a temperature sensitive BAC containing a segment of DNA of a test cell to create a merodiploid cell. A transposon is introduced into an essential gene of the *E. coli* within the region of host chromosomal DNA having homology with the segment of DNA of the test cells. Incubation of the merodiploid cell at 30° C. does not affect viability, but incubation at 43° C. kills the temperature sensitive BAC. Death of the merodiploid cell indicates that the transposon disrupted an essential gene in the *E. coli* DNA causing death of the host cell.
Figure 2:
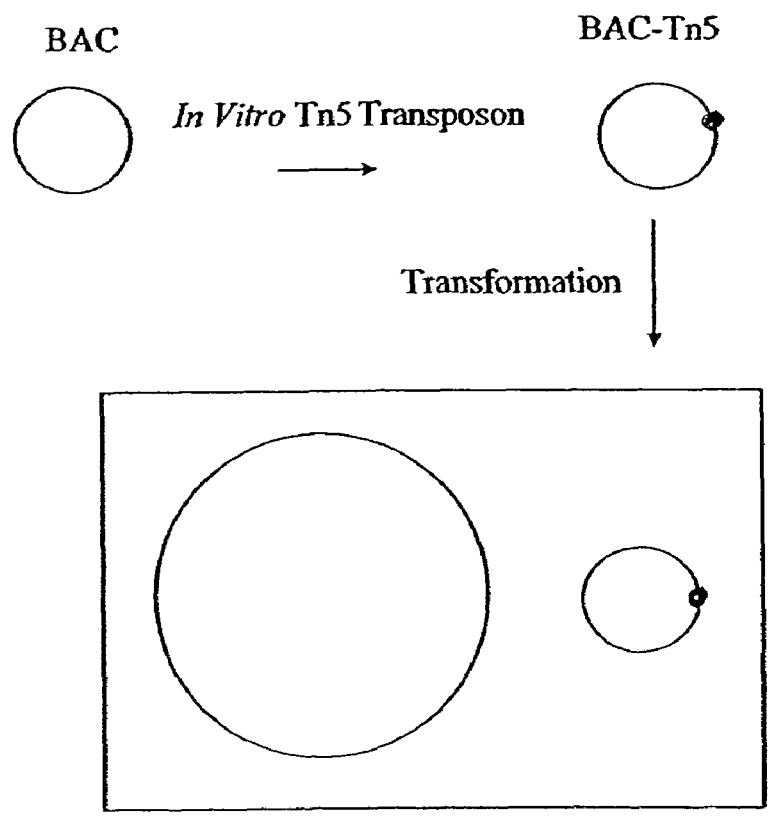
FIG. 2 is a schematic diagram showing preparation of a merodiploid test cell using a BAC (medium-sized open circle) into which Tn5 (shown as a small dark circle) is randomly inserted to form BAC-Tn5. A host cell (shown as a square with a large open circular chromosomal DNA) is then transformed with BAC-Tn5.

A new method has been developed, as described here, to identify and determine genes that are essential for growth of prokaryotes. *Escherichia coli*, one of the most extensively studied prokaryotes, is used as a model microorganism. The essential genes are genes required for synthesis of macromolecules such as proteins, RNA and DNA; for construction of cell wall, membrane, ribosomes and other structural components; and for other survival functions. Functional loss of any of these genes causes growth inhibition even in nutrient rich media, and even eventual cell death. Genes for synthesis of amino acids, vitamins and other organic/inorganic materials are generally not essential genes. Since these small compounds are readily found in nutrient rich media, defective genes for these nutrient syntheses do not lead to cell death.

The present invention is based on the knowledge that during evolution the essential genes in most of the prokaryotic microorganisms are conserved as analogous genes (orthologs) in their genomes. Therefore, for example, the essential genes found in *E. coli* are very similar, i.e., homologous, to the corresponding essential gene in a variety of other bacterial species, including bacterial pathogens. As a result, *E. coli*, or another of the prokaryotic microorganisms whose genome has been completely mapped, can be used as a framework to develop antibiotics that act with broad spectrum and high efficacy by inactivation of an essential gene or essential gene product common to a variety of pathogenic bacteria. Because the target proteins are coded by genes indispensable to cell growth, antibiotics to be developed using the invention methods disclosed herein will generally be bactericidal rather than bacteriostatic. The proteins coded for by the essential genes of one prokaryote are ideal target molecules for identification and development of antibiotics against diploid infectious bacterial pathogens.

Prokaryotic organisms, such as *E. coli*, are haploid cells (one copy chromosome per cell) while they are not replicating. Consequently, when a potentially lethal mutation by transposon insertion occurs in one of the essential genes, the resultant prokaryotic cell dies, making it impossible to recover the mutated bacteria as a viable cell for identification and analysis of the essential gene discovered by knockout. The difficulty posed by this phenomenon is overcome in the invention method by providing to the test cell an additional copy of the gene that will be knocked out before the mutation occurs. Thus, the second gene can supply the normal function, and the cell can survive despite the presence of the lethal mutation.

The invention methods, as described herein, employ two key technologies; a bacterial transposon, such as Tn10 or Tn5, for knockout mutagenesis and the BAC (Bacterial Artificial Chromosome) cloning system for constructing partially diploid cells (merodiploids) or for transferring a knocked out gene in a segment of DNA whose sequence is known from the BAC to a host cell. A transposon is a DNA molecule that is capable of integrating into a target DNA molecule, without sharing homology with the target DNA molecule. The target molecule may be, for example, chromosomal DNA, cloned DNA, or PCR-amplified DNA. Transposon integration is catalyzed by transposase enzyme, which may be encoded by the transposon itself, or may be exogenously supplied. One example of a transposon is mariner. Other examples include Tn5, Tn7 and Tn10. In the present invention, the transposon is used to inactivate normal function of a gene by insertion and by subsequent disruption of the correct reading frame of the gene. The insertion occurs randomly on host cell chromosome or in the segment of test cell DNA contained in a BAC and any insertion in a gene makes the gene nonfunctional.

Accordingly, in one embodiment according to the present invention, there are provided methods for identifying an essential gene in a haploid test organism. In the invention method a BAC-carrying merodiploid test cell is constructed by transforming a wild-type haploid host cell with a bacterial artificial chromosome (BAC) carrying a known segment of DNA of the haploid test organism carrying a segment of DNA of the haploid test organism, which segment is homologous to a known segment of chromosomal DNA in the host cell, and wherein replication of the BAC in the test cell is sensitive to an environmental condition that selectively prevents replication of the BAC in the host cell, inserting randomly a bacterial transposon into the merodiploid test cell so as to disrupt function of a gene therein, and culturing one or more of the BAC-carrying merodiploid test cells in a suitable culture medium while introducing the environmental condition so as to transform the merodiploid test cells into haploid test cells. The invention method further comprises identifying one or more of the haploid test cells containing transposon-mutagenized DNA of an essential chromosomal gene and obtaining the essential chromosomal gene by homology with a gene in the known segment of DNA. For example, test cells that contain a trasposon-mutagenized essential chromosomal gene do not grow in or survive subjection to growth conditions that are non-permissive to growth of the BAC contained therein.

It is an important feature of the invention methods that the merodiploid host cell(s) are engineered to contain a BAC with a segment of DNA that corresponds to (i.e., is homologous to) a known segment of chromosomal DNA of the host cell. Homology between corresponding segments of host cell and test organism DNA is typically in the range from about 80% sequence identity to about 100% sequence identity, for example, 85% identity, 90% identity or 95% identity. Sequence correspondence (i.e., homology as described above) between the segment of DNA placed into an individual BAC and a particular segment of chromosomal DNA of the host cell is established prior to construction of the merodiploid cells. For convenience, therefore, the host cell is preferably a prokaryotic cell whose entire genome has been mapped so that the location of each gene therein is known.

Due to the high degree of sequence conservation in essential genes among haploid organisms, the same organism can be used both as host cell and as provider of the various segments of DNA that are inserted into the BACs. Alternatively, two different species of haploid organism can be used as host cell and as provider of the various segments of DNA that are inserted into the BACs used in the invention methods. Preferred host cells for use in constructing the merodiploid cells used in the invention methods are *E. coli, Salmonella*, and *B. subtilis*, with *E. coli* being most preferred due to the extensive knowledge of its genome.

In one embodiment according to the present invention, the BACs are introduced into the host cells in vivo using known methods for transforming live cells with a plasmid. For example, the BAC may be first introduced into a cosmid/fosmid and then the cosmid/fosmid introduced directly into the host cell. Alternatively, the cosmid/fosmids may be packaged into a phage for efficiency of cloning in the host cells. A preferred phage for this purpose is lambda phage. When the BACs are introduced into the host cells in vivo to create a merodiploid cell, the transposon is randomly introduced into the completed merodiploid cell and may insert itself into any location in the BAC or in the host cell.

To make removal of the BAC from the merodiploid test cell conditional, it is preferred to utilize a mutant BAC that is engineered to be replication sensitive in maintenance. Such a replication sensitive mutant is readily eliminated from the cell by providing the condition to BAC is replication sensitive, e.g. a non-permissive temperature or a replication suppressor. When this happens, if the transposon disrupts an essential gene in host cell chromosomal DNA, the cell dies due to the loss of the undisrupted essential gene contained within its replication sensitive BAC.

Therefore, in this embodiment of the invention, the BACs are engineered to be sensitive to an environmental condition, such that culture of the BAC-containing host cell under the environmental condition prevents or inhibits replication of the BAC without killing the host cell. In a preferred embodiment, the BAC may contain an origin of replication having a mutation which makes its functioning temperature-sensitive in the host cell. See, for example, Ehrlich, *Proc. Natl. Acad. Sci. USA* (1978) 75:1433. As used herein, a BAC containing such a mutation is referred to as being "temperature sensitive to replication." During replication of the BAC-containing host cell at the permissive low temperature, for example 30° C. to 34° C., the BAC remains viable in the host cell, but when the temperature is elevated to a non-permissive temperature, for example 45° C., the BAC ceases to replicate and is lost from the host cell. See also U.S. Pat. No. 5,925,544, which is incorporated herein by reference in its entirety.

To aid in determining whether the transposon inserts into an essential chromosomal gene of the host cell, the transposon is preferably operably linked with a DNA sequence encoding a first phenotypically selectable marker prior to its random insertion into the merodiploid cell. By "selectable marker" is meant a gene that alters the ability of a cell harboring the transposon to grow or survive in a given growth environment relative to a similar cell lacking the selectable marker. Such a marker may be a positive or negative selectable marker. For example, a positive selectable marker (e.g., an antibiotic resistance or auxotrophic growth gene) encodes a product that confers growth or survival abilities in selective medium (e.g., containing an antibiotic or lacking an essential nutrient). A negative selectable marker, in contrast, prevents transposon-harboring cells from growing in negative selection medium, when compared to cells not harboring the transposon. A selectable marker may confer both positive and negative selectability, depending upon the medium used to grow the cell. The use of selectable markers in prokaryotic cells is well known by those of skill in the art.

Examples of such selectable markers that can be used for this purpose in prokaryotic cells include antibiotic resistance genes for ampicillin (β-lactamases), tetracycline, kanamycin, and chloramphenicol (chloramphenicol acetyltransferase). DNA encoding a second phenotypically selectable marker can be included in the BAC such that the first and second markers are selected to be sensitive to two different environmental conditions. Preferably, a second, different, antibiotic resistance gene is included in the BAC to allow for determination of whether the host cell has been successfully transformed with a replication sensitive BAC. In practice of the invention method wherein two different antibiotic resistance genes are used to distinguish clones that contain a transposon and a BAC, the identifying includes sequentially subjecting the test cells during culture to the first antibiotic and then to the second antibiotic to which the antibiotic resistance genes provide resistance.

In this embodiment of the invention, determination of tests cells wherein an essential gene in host chromosomal DNA has been "knocked out" depends upon the BAC being engineered to be replication sensitive to cause loss of the BAC contained within the merodiploid test cells by subjecting the test cells to an environmental condition to which the BAC has been engineered to be replication sensitive. By this means, it is readily determined whether loss of the BAC results in a lethal phenotype. When the test cells are grown at an elevated non-permissive temperature under conditions that allow rapid detection of test cell viability, viability of a test cell (despite loss of the replication sensitive BAC by its failure to replicate under non-permissive conditions) is strong evidence that the randomly inserted transposon did not become inserted into an essential gene in test cell chromosomal DNA. Conversely, test cells that are killed under these conditions are identified as having had an essential gene in chromosomal DNA disrupted by the transposon. Due to the known homology between the segment of DNA contained in the BAC and the corresponding segment of host chromosomal DNA, the exact location of the essential gene in the prokaryotic genome is readily obtained, for example using various mapping methods known in the art.

In another embodiment according to the invention, there are provided methods for identifying an essential gene in a haploid organism, for example a pathogenic bacterium, wherein the transposon is randomly introduced into the BAC before the BAC is introduced into the host cell. In this embodiment of the invention methods, the transposon is randomly inserted into the BAC in vitro (either at the time the known segment of DNA is inserted into the BAC to form a transposon-containing BAC (BAC-Tn) or thereafter). By this process, which is sometimes referred to in the art as "in vitro transposition," the transposon integrates into the known segment of DNA (e.g., the target DNA) in a non-living cell. In an in vitro transposition reaction, the transposon integrates into the target DNA randomly, or with near randomness; that is, all DNA regions in the known segment of DNA have approximately equal chances of being sites for transposon integration.

In at least some of the BAC-Tns so constructed, a knockout gene is formed within the known segment of DNA inserted into the BAC-Tn and the BAC-Tn is used as an "allelic replacement vector" to introduce mutations into the genome of a host cell by specific replacement of a gene in the chromosome of the host cell with a mutated (i.e., knockout) copy. The BAC-Tn integrates into the host cell's chromosome by homologous recombination (single crossover) in a region where there is identical or near-identical nucleotide sequence between the two molecules. Homologous recombination is mediated by complementary base-pairing, and may result in either insertion of the exogenous DNA into the host target DNA (a single cross-over event), or replacement of the host target DNA by the exogenous DNA (a double cross-over event).

Preferably, the BAC-Tn contains a negative selectable marker outside of the region of homology, appropriate selection yields cells that have lost the negative selection marker by a second homologous recombination event (double cross-over) and contain only a mutant copy of the essential gene. Thus, recombination during replication is used to replace a gene in the host cell chromosome with its homologous knockout gene provided on the BAC-Tn. If the test cell does not survive in culture, it is identified as having had inserted into its chromosomal DNA a segment of DNA from its respective BAC-Tn wherein an essential gene was disrupted by the transposon. Using this information and the knowledge of the particular segment of test organism DNA that was introduced into this particular test cell, the identity of the essential gene is readily obtained using known methods. Preferably, the BAC-Tn is engineered to be antibiotic resistant so that selection of antibiotic resistant clones will indicate test cells wherein the transposon did not insert into an essential gene (although upon recombination antibiotic resistance was conferred upon the test cell).

Unlike prior art methods for detection of essential genes in prokaryotes, in the invention method a complete gene is knocked out and means is provided for identifying the location in the genome of the test prokaryotic organism of the knocked-out gene. In a preferred embodiment, the invention method is used to identify virtually all of the essential genes in *E. coli*.

In host cells such as *E. coli*, a BAC containing up to 350 kb of prokaryotic DNA can exist as a large plasmid. Thus, more than 100 genes of *E. coli* may be investigated in a single BAC clone. Since there are about 4,289 open reading frames in *E. coli* chromosome, construction of only 50 to 100 merodiploid test cells containing different segments of the host cell DNA may be sufficient to complete the identification of the essential genes by the invention method.

In a preferred embodiment according to the present invention, the entire genome of the test organism is used in construction of the BACs such that a library of merodiploid host cells collectively contains the entire genome of the test organism is constructed for testing according to the invention method. For this purpose, it is preferred to shear the genome of the test organism to prepare blunt-ended segments having a very random distribution. The insertions can be verified and localized by sequencing, PCR, Southern blot, cloning without restriction digests using terminal transferase, and the like.

For building a library of knock-out mutants, non-limiting examples of two *E. coli* strains that can be used experimentally as described herein, and that can be compared with respect to experimental results include: *E. coli* MG1655 (rph-1)($r_k$+$m_k$+) and JM101 (supE thi-1 $r_k$+$m_k$+δ(lac-proAB)[F' traD36 proAB lacI$^q$ZδM15].

To analyze the nature of insertion distribution throughout the genome one can map the mutations on an *E. coli* matrix. The overall distribution may be random and the transposed loci may be scattered (tranposition process is relatively random) with defined clustering of the related mutations (selection is biased) indicating a high density of sequential insertions.

If desired, a complete knockout library can be built, archived and made available in different formats. Preferably, to allow for statistical analysis of the results obtained by the invention methods, sufficient of the merodiploid test cells are constructed to provide at least quadruple coverage of the entire genome of the haploid test organism. Using the invention methods, one can sequence and archive enough mutants to reach complete saturation of a genome (or part of a genome).

Many of the gram-positive bacterial pathogens are diploid organisms. Thus, the invention methods can be used for screening bacterial genes in a pathogenic bacterium whose genome is known to select compounds with putative antibiotic activity. In this embodiment, the invention screening methods comprise constructing BAC-carrying merodiploid test cells as described above wherein a known segment of DNA of a pathogenic diploid bacterium is contained within the BACs. The invention screening methods further comprise obtaining the identity of a corresponding essential gene in the pathogenic bacterium by homology with the identified essential chromosomal gene in the host cell, and screening the corresponding essential gene obtained from the pathogenic bacterium or a bacterial protein encoded by the essential gene against putative antibiotic compounds to determine those compounds that bind to or interrupt function of the essential gene or the bacterial protein encoded thereby. Such a compound is a candidate antibiotic against the pathogenic bacterium and may include small molecules, a protein or polypeptides or a polynucleotide.

Illustrative pathogenic positive bacterium that can be screened to identify essential genes therein using the invention methods include such organisms as *Actinobacillus actinomycetemcomitans; Borrelia burgdorferi; Chlamydia trachomatis; Enterococcusfaecalis; Escherichia coli; Haemophilus influenzae; Helicobacter pylori; Legionella pneumophila; Mycobacterium avium; Mycobacterium tuberculosis; Mycoplasma genitalium; Mycoplasma pneumonia; Neisseria gonorrhoeae; Neisseria meningitidis; Staphylococcus aureus; Streptococcus pneumoniae; Streptococcus pyogenes; Treponema pallidum; Vibrio cholerae,* and the like.

By "homology" is meant sequence similarity between two peptides or between two nucleic acid molecules. Homology can be determined by comparing the residues in positions in two sequences, which may be aligned for purposes of comparison. When a position in the compared sequence is occupied by the same base or amino acid as the sequence to which it is compared, then the molecules are homologous at that position. Percent homology between sequences is a function of the number of matching or homologous positions shared by the sequences.

The sequence data of a test clone is aligned to the sequences in the database or databases using algorithms designed to measure homology between two or more sequences. Sequence alignment methods include, for example, BLAST (Altschul et al., 1990), BLITZ (MPsrch) (Sturrock & Collins, 1993), and FASTA (Person & Lipman, 1988). For example, optimal alignment of sequences for aligning a comparison window may be conducted by the local homology algorithm of Smith (Smith and Waterman, Adv Appl Math, 1981; Smith and Waterman, J Theor Biol, 1981; Smith and Waterman, J Mol Biol, 1981; Smith et al, J Mol Evol, 1981), by the homology alignment algorithm of Needleman (Needleman and Wunsch, 1970), by the search of similarity method of Pearson (Pearson and Lipman, 1988), by computerized implementations of these algorithms (GAP, BESTFIT, FASTA, and TFASTA in the Wisconsin Genetics Software Package Release 7.0, Genetics Computer Group, 575 Science Dr., Madison, Wis., or the Sequence Analysis Software Package of the Genetics Computer Group, University of Wisconsin, Madison, Wis.), or by inspection, and the best alignment (i.e., resulting in the highest percentage of homology over the comparison window) generated by the various methods is selected.

By "permissive growth conditions" or "rich growth conditions" is meant an environment that is relatively favorable for cell growth and/or viability. Such conditions take into account the relative availability of nutrients, the absence of toxins, and optimal temperature, atmospheric pressure, presence or absence of gases (such as oxygen and carbon dioxide), and exposure to light, as required by the organism being studied. Permissive growth conditions may exist in vitro (such as in liquid and on solid culture media) or in vivo (such as in the natural host or environment of the cell being studied).

By "non-permissive growth conditions" is meant an environment that is relatively unfavorable for growth and/or viability of cells of an organism. An unfavorable environment may be due to nutrient limitations (e.g., as seen with "minimal" bacterial growth medium such as MIc), the presence of a compound that is toxic for the cell under study, an environmental temperature, gas concentration, light intensity, or atmospheric pressure that is extreme (e.g., either too high or too low) for optimal growth/viability of the organism under study.

By "gene that is essential for growth and/or viability" or by "essential gene" or by "essential gene in a known segment of DNA" is meant a DNA element such as an origin of replication or a gene that encodes a polypeptide or RNA whose function is required for survival, growth, or mitosis/meiosis of a cell. Insertion of a transposon into an essential gene may be lethal, i.e., prevent a cell from surviving, or it may prevent a cell from growing or undergoing mitosis/meiosis. Alternatively, insertion of a transposon into an essential gene may allow survival of a cell, but result in severely diminished growth or metabolic rate. An essential gene also may be conditionally essential (i.e., required for viability and/or growth under certain conditions, but not under other conditions).

By "absence of transposons" is meant that fewer transposon insertions are detected in an essential region of DNA, relative to the number of transposon insertions detected in a non-essential region of DNA. An absence of transposons may be absolute (i.e., zero transposons detected) or relative (i.e., fewer transposons detected).

By "transformation" or "transforming" is meant any method known in the art for introducing foreign molecules, such as DNA, into a cell. Lipofection, DEAE-dextran-mediated transfection, microinjection, protoplast fusion, calcium phosphate precipitation, retroviral delivery, electroporation, natural transformation, and biolistic transformation are just a few of the methods known to those skilled in the art which may be used. For example, biolistic transformation is a method for introducing foreign molecules into a cell using velocity driven microprojectiles such as tungsten or gold particles. Such velocity-driven methods originate from pressure bursts that include, but are not limited to, helium-driven, air-driven, and gunpowder-driven techniques.

By "identifying cells containing transposon-mutagenized DNA of an essential gene" is meant exposing the population of cells transformed with transposon-mutagenized DNA to selective pressure (such as growth in the presence of an antibiotic or the absence of a nutrient) consistent with a selectable marker carried by the transposon (e.g., an antibiotic resistance gene or auxotrophic growth gene known to those skilled in the art). Identifying cells containing mutagenized DNA may also be done by subjecting transformed cells to a reporter gene assay for a reporter gene product encoded by the transposon. Selections and screens may be employed to identify cells containing mutagenized DNA, although selections are preferred.

It will be understood by those of skill in the art that the "detectable genes" disclosed herein can be replaced by any gene which encodes a product whose expression is detectable and/or quantitatable by immunological, chemical, biochemical, biological, or mechanical assays. A reporter gene product may, for example, have one of the following attributes, without restriction: fluorescence (e.g., green fluorescent protein), enzymatic activity (e.g., lacZ/β-galactosidase, luciferase, chloramphenicol acetyltransferase, alkaline phosphatase), toxicity (e.g., ricin), or an ability to be specifically bound by a second molecule (e.g., biotin or a detectably labelled antibody). It is understood that any engineered variants of reporter genes, which are readily available to one skilled in the art, are also included, without restriction, in the foregoing definition.

By "obtaining an essential gene in a segment of DNA" is meant determining that a given stretch of DNA contains a gene that is necessary for cell growth and/or viability and locating the essential gene within the segment of DNA. Such a gene may be necessary under all, or only under some (e.g., stringent) growth conditions. The locating may be done, for example, by such techniques as PCR footprinting, by utilizing primers to obtain copies by PCR and compare the copies of genes in the segment of DNA with wild type genes in the host cell, and the like.

The invention provides a method for the rapid identification of essential or conditionally essential DNA segments. The method is applicable to any species of haploid cell (one copy chromosome per cell) that is capable of being transformed by artificial means and is capable of undergoing DNA recombination. This system offers an enhanced means of identifying essential function genes in pathogens, such as gram negative and gram-positive bacteria.

The invention will be further described with reference to the following examples; however, it is to be understood that the invention is not limited to such examples.

EXAMPLE 1

Merodiploid cells test cells were prepared using $E.$ $coli$ as host cell and as provider of DNA segments that were inserted into bacterial artificial chromosomes that were engineered to be temperature sensitive for replication (BACts). The $E.$ $coli$ host cells were transformed with the BACts and then the merodiploid cells were randomly transformed in vivo with Tn5 transposon. Following insertion of Tn5 into the merodiploid cells, six different clones could be expected, as shown in Table 1 below, depending on the insertion location of Tn5 in the merodiploid test cells. The BACts and the transposon, Tn5, were tagged by Chloramphenicol (Cm) and Kanamycin (Km) resistance markers, respectively. The drug resistance markers were used to detect the presence of BACts and Tn5 in the transformed cells.

TABLE 1

| Clone Types | Location of Tn5 Transposon | Growth at 30 C on LB + KM + Cm plate | Growth at 43 C on LB + Km plate | Growth at 43 C on LB plate (No drug) | 43 C + Cm |
|---|---|---|---|---|---|
| A.  E. coli DNA | No Transposon | No | No | Yes | No |
| B.  | Transposon in non-essential gene outside BAC homology region | Yes | Yes | Yes | No |
| C.  | Transposon in essential gene outside BAC homology region | No | No | No | No |
| D.  | Transposon in essential gene inside BAC homology region | Yes | Yes | Yes | No |
| E  | Transposon in essential gene inside BAC homology region | Yes | No | No | No |
| F  | Transposon in BAC | Yes | No | Yes | No |

For illustration purpose, only the BAC segment homologous to E. coli chromosome is shown in a linear form with two connecting lines to E. coli chromosome in the diagram. Insertion location of Tn5 = ☆

Thus, the six different types of clones can be differentiated by colony formation in the absence or presence of drugs in Luria broth (LB) media and by the temperature change from 30° C. to 43° C. For example, clone D can grow in the presence of Km and Cm at both 30° C. and 43° C., indicating that the clone D has Tn5 inserted in a non-essential gene of E. coli. On the other hand, clone E and F can grow in the presence of both Km and Cm only at 30° C., and the clones cannot grow at 43° C. in the presence of Km. An ability to grow at 43° C. without the drugs distinguish the two clones, indicating that Clone F has Tn5 in BACts and clone E has Tn5 in the essential gene in E. coli chromosome. For identification of the essential genes, type E clones were collected and stored.

BLAST searches were conducted to compare wild-type host DNA with chromosomal DNA of the type E clones to determine the location of the mutagenized essential genes. These clones will be used for characterization of the essential genes. The proteins encoded by each wild-type essential gene can then be produced in large amounts for antibiotic screening and development.

EXAMPLE 2

In an alternative method for preparation and screening of merodiploid BAC-carrying test cells, Tn5 was inserted into the BACts to create a temperature sensitive BAC designated BAC-Tn5. General recombination during replication is used to replace a gene in the E. coli chromosome with its homologous knockout gene on BAC-Tn5. If the knockout gene in the BAC-Tn5 is not essential, the replacement becomes successful upon transformation, presenting viable Km resistant colonies. On the other hand, if the knockout occurred in an essential gene, when replacement is completed by recombination, it leads to no production of Km resistant colony. In this way, one can identify essential genes by scoring Km resistant colonies.

Figure 3:
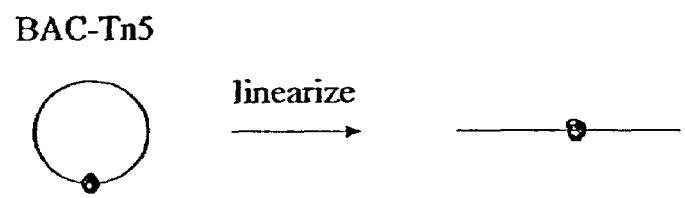
FIG. 3 is a schematic diagram illustrating linearization of BAC-Tn5 in preparation for insertion into a host cell by electroporation.

In this method the BAC-Tn5 was constructed by insertion of Tn5 into the BAC in vitro, instead of transposing Tn5 onto BAC in vivo as described above in Example 1. The resultant BAC-Tn5 was used to transform E. coli. This process is illustrated in FIG. 3. In this protocol, each BAC-Tn5 already contains a Tn5 inserted therein in random fashion before transformation of the host cells (i.e. E. coli). In addition, and unlike the method described in Example 1 above, there is only one type of Km resistant clone for each Km resistant cell, a clone containing a knockout gene on BAC-Tn5 and its normal allele on the host chromosome.

Although the method examines each BAC-Tn5 to identify essential genes on the BAC, whole genome-wide search is also possible. It involves a construction of BACTn5 without having individual BAC clones prior to introducing Tn5. This is accomplished by transposing Tn5 in vitro at the time of ligating the various segments of test organism DNA that represent the entire genome of the test organism into the BAC vectors (in this case known segments of E. coli DNA).

Figure 4:
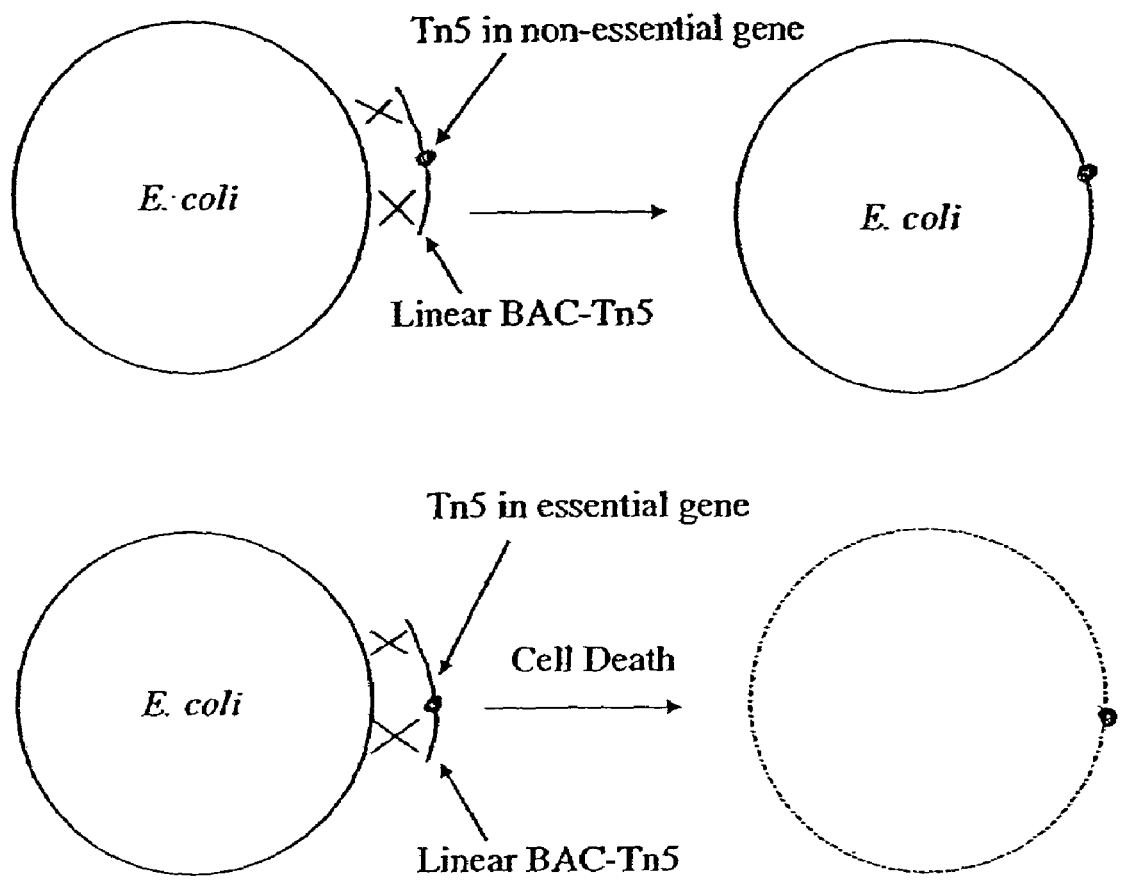
FIG. 4 is a schematic diagram comparing two outcomes of insertion of the linearized BAC-Tn5t into *E. coli*. In the top representation BAC-Tn5 does not contain a mutation in an essential gene and the host cell survives replacement of genomic DNA by homologous DNA in BAC-Tn5. In the bottom scheme BAC-Tn5 does contain a mutation in a gene that corresponds to an essential gene in host chromosomal DNA and the host cell does not survive replacement of its genomic DNA by homologous DNA in BAC-Tn5.

In order to increase the number of transformants formed by double crossover recombination, and to decrease the frequency of recombinants formed by reciprocal Campbell type recombination, BAC-Tn5 DNA is linearized, the plasmid is removed, and *E. coli* host in which the recombination is carried out is a RecBC-SbcBC quadruple mutant (FIG. 4).

Although the invention has been described with reference to the above examples, it will be understood that modifications and variations are encompassed within the spirit and scope of the invention. Accordingly, the invention is limited only by the following claims.

What is claimed is:

1. A method for identifying an essential chromosomal gene in a haploid test organism, said method comprising:
   a) constructing a bacterial artificial chromosome (BAC)-carrying merodiploid test cell by transforming a wild-type haploid host cell whose genomic sequence is known, which is naturally capable of being transformed and undergoing DNA recombination, with a BAC carrying a known segment of DNA of the haploid test organism with about 80% to 100% sequence identity to a known segment of chromosomal DNA in the host cell, and wherein replication of the BAC in the test cell is sensitive to an environmental condition that selectively prevents replication of the BAC in the host cell;
   b) inserting randomly a bacterial transposon into the merodiploid test cell so as to disrupt function of a gene therein;
   c) culturing one or more of the BAC-carrying merodiploid test cells in a suitable culture medium while introducing the environmental condition so as to transform the merodiploid test cells into haploid test cells;
   d) identifying one or more of the haploid test cells that contain transposon-mutagenized DNA in an essential chromosomal gene therein, and
   e) obtaining the identity of the essential chromosomal gene in the test organism by locating a gene in the known segment of DNA of the haploid test organism that contains the transposon-mutagenized DNA.

2. The method of claim 1 wherein the identifying of d) comprises selection of test cells that do not survive subjection to the environmental condition as having the transposon in an essential chromosomal gene therein.

3. The method of claim 1, wherein the transposon is Tn5 or Tn10.

4. The method of claim 3, wherein the transposon is operatively linked to a first antibiotic resistance gene.

5. The method of claim 4, wherein the BAC comprises a second antibiotic resistance gene, wherein the first and second antibiotic resistance genes convey resistance to two different antibiotic compounds.

6. The method of claim 5, wherein the first and second antibiotic resistance genes are selected to provide resistance to a pair of antibiotics selected from the group consisting of ampicillin, tetracycline, kanamycin, and chloramphenicol.

7. The method of claim 6, wherein the first and second antibiotic resistance genes provide resistance, respectively, to kanamycin and chloramphenicol.

8. The method of claim 5, wherein identifying one or more of the haploid test cells that contain transposon-mutagenized DNA in an essential chromosomal gene therein includes subjecting the test cells to both of the antibiotics to which the first and second antibiotic resistance genes provide resistance.

9. The method of claim 1, wherein the BAC is temperature sensitive for replication and the environmental condition is a temperature that is non-permissive for replication of the BAC in the test cell.

10. The method of claim 1, wherein the BAC is suppressor sensitive for replication and the environmental condition is a suppressor that selectively suppresses replication of the BAC in the test cell.

11. The method of claim 1, wherein the host cell is selected from the group consisting of *E. coli, Salmonellae,* and *B. subtilis.*

12. The method of claim 11, wherein the host cell is *E. coli.*

13. The method of claim 1, wherein the identified essential chromosomal gene has 100% sequence identity with a gene in the known segment of DNA from the haploid host cell.

14. The method of claim 1, wherein the identified essential chromosomal gene has at least 90% sequence identity with a gene in the known segment of DNA from the haploid host cell.

15. The method of claim 1, wherein the identified essential chromosomal gene has at least 80% sequence identity with a gene in the known segment of DNA from the haploid host cell.

16. The method of claim 1, wherein the BAC contains up to 100 genes of the haploid test organism.

17. The method of claim 1, wherein the haploid test organism and the host cell are the same species of prokaryote.

18. The method of claim 1, wherein a library of the BAC-carrying merodiploid test cells is constructed such that the BACs in the library collectively contain the entire genome of the haploid test organism.

19. The method of claim 18, wherein the entire genome of the haploid organism is contained in about 50 to 100 merodiploid test cells that each contain a unique segment of the genome of the haploid test organism.

20. The method of claim 18, wherein the test cells in the library are simultaneously subjected to the environmental condition.

21. The method of claim 1, wherein sufficient of the merodiploid test cells are constructed to provide four-fold coverage of the entire genome of the haploid organism.

22. The method of claim 1, wherein the BAC in the merodiploid test cell is contained within a fosmid/cosmid.

23. The method of claim 22, wherein the fosmid/cosmid is packaged in lambda phage prior to transformation of the haploid host cell.

24. A method of screening compounds for putative antibiotic activity against a pathogenic bacterium whose genome is known, said method comprising:
   a) constructing a BAC-carrying merodiploid test cell by transforming a wild-type haploid host cell whose genomic sequence is known, which is naturally capable of being transformed and undergoing DNA recombination with a BAC that carries a known segment of DNA of a haploid pathogenic bacterium, and wherein the BAC in the test cell is sensitive to an environmental condition that selectively prevents replication of the BAC in the test cell;
   b) inserting randomly a transposon into the merodiploid test cell so as to disrupt function of a gene therein;
   c) culturing one or more of the merodiploid test cells in a culture medium suitable for viability of a wild-type haploid test cell, while further introducing the environmental condition;

d) identifying one or more test cells that do not survive subjection to the environmental condition as containing the transposon in an essential chromosomal gene therein;

e) locating the essential gene in the pathogenic bacterium by identifying a gene in the known segment of DNA of the pathogenic bacterium inserted into the test cell by the BAC that has been disrupted by the transposon; and f) screening the essential gene from the pathogenic bacterium or a bacterial protein encoded by the essential gene against putative antibiotic compounds to determine those compounds that bind to or interrupt function of the essential gene or the bacterial protein, wherein such a compound is a candidate antibiotic against the pathogenic bacterium.

25. The method of claim 24, wherein the transposon is Tn5 or Tn10.

26. The method of claim 24, wherein the transposon is operatively linked to a first antibiotic resistance gene.

27. The method of claim 26, wherein the BAC comprises a second antibiotic resistance gene.

28. The method of claim 27, wherein the first and second antibiotic resistance genes are selected to provide resistance to a pair of antibiotics selected from the group consisting of ampicillin, tetracycline, kanamycin, and chloramphenicol.

29. The method of claim 28, wherein the first and second antibiotic resistance genes provide resistance, respectively, to kanamycin and chloramphenicol.

30. The method of claim 28, wherein the locating includes subjecting the test cells to the antibiotics to which the first and second antibiotic resistance genes provide resistance.

31. The method of claim 24, wherein the BAC is temperature sensitive and the environmental condition is a non-permissive temperature for replication of the BAC in the test cells.

32. The method of claim 24, wherein the BAC is suppressor sensitive and the environmental condition is a suppressor that selectively prevents replication of the BAC in the test cells.

33. The method of claim 24, wherein the host cell is selected from the group consisting of E. coli, Salmonellae, and B. subtilis.

34. The method of claim 33, wherein the host cell is E. coli.

35. The method of claim 24, wherein the BAC contains up to 100 genes of the pathogenic bacterium.

36. The method of claim 24, wherein a library of the BAC-carrying merodiploid test cells is prepared such that the BACs in the library collectively contain the entire genome of the pathogenic bacterium.

37. The method of claim 36, wherein the entire genome is contained in about 50 to 100 merodiploid test cells that each contain a unique segment of the genome of the pathogenic bacterium.

38. The method of claim 37, wherein the test cells in the library are simultaneously subjected to the environmental condition.

39. The method of claim 24, wherein the candidate antibiotic is bactericidal.

40. The method of claim 24, wherein the bacterium is pathogenic in at least one mammalian species.

41. The method of claim 24, wherein the bacterium is pathogenic in at least one plant species.

42. A method for identifying an essential chromosomal gene in a haploid test organism, said method comprising:

a) constructing a BAC carrying a known segment of DNA of the haploid test organism with about 80% to 100% sequence identity to a known segment of chromosomal DNA in a haploid host cell having a known genomic sequence, which is naturally capable of being transformed by artificial means and undergoing DNA recombination with the BAC;

b) inserting randomly a bacterial transposon into the BAC so as to disrupt function of a gene in the segment of chromosomal DNA;

c) introducing the BAC into the haploid host cell to create a merodiploid test cell;

d) culturing the merodiploid test cell in a suitable culture medium while introducing an environmental condition that selectively prevents replication of the BAC in the test cell;

e) identifying one or more BAC-carrying merodiploid test cells that do not survive in culture as containing the transposon in an essential chromosomal gene therein; and f) obtaining the identity of the essential chromosomal gene by determining which gene in the known segment of DNA of the haploid test organism inserted into the BAC was disrupted by the transposon.

43. The method of claim 42, wherein the transposon is Tn5 or Tn10.

44. The method of claim 42, wherein the transposon is operatively linked to a first antibiotic resistance gene.

45. The method of claim 42, wherein the transposon is inserted randomly into the BAC in vitro prior to introduction of the BAC into the haploid host cell.

46. The method of claim 45, wherein the BAC is linearized prior to introduction into the host cell.

47. The method of claim 42, wherein the host cell is an E. coli RecBC-SbcBC quadruple mutant.

48. The method of claim 42, wherein the identifying includes subjecting the test cells to the antibiotic to which the antibiotic resistance gene provides resistance.

49. The method of claim 42, wherein the host cell is selected from the group consisting of E. coli, Salmonellae, and B. subtilis.

50. The method of claim 42, wherein the BAC contains up to 100 genes of the test organism.

51. The method of claim 42, wherein a library of the BAC-carrying merodiploid test cells is prepared such that the BACs in the library collectively contain the entire genome of the test organism.

52. The method of claim 51, wherein the entire genome is contained in about 50 to 100 merodiploid test cells that each contain a unique segment of the genome of the test organism.

53. The method of claim 42, wherein the test organism is a pathogenic bacterium.

54. The method of claim 53, wherein the method further comprises screening the essential gene from the pathogenic bacterium or a bacterial protein encoded thereby against putative antibiotic compounds to determine those compounds that bind to or interrupt function of the essential gene or the bacterial protein, wherein such a compound is a candidate antibiotic against the pathogenic bacterium.

* * * * *